(12) United States Patent
Wang

(10) Patent No.: US 6,260,208 B1
(45) Date of Patent: Jul. 17, 2001

(54) COLLAPSIBLE VISOR FOR HEAD WEAR

(76) Inventor: Grace Wang, 828 W. Cienega Ave., #2, San Dimas, CA (US) 91773

( * ) Notice: Subject to any disclaimer, the term of this patent is extended or adjusted under 35 U.S.C. 154(b) by 0 days.

(21) Appl. No.: 09/415,257

(22) Filed: Oct. 12, 1999

(51) Int. Cl.$^7$ ..................................................... A42B 1/00
(52) U.S. Cl. ........................................... 2/209.11; 2/171.03
(58) Field of Search .................................... 2/209.11, 171, 2/171.4, 171.8, 183, 209.12, 175.1, 195.1, 195.5, 195.6

(56) References Cited

U.S. PATENT DOCUMENTS

| 1,609,715 | * | 12/1926 | Hess | 2/209.11 |
| 2,495,041 | * | 1/1950 | Weiss | 2/209.11 |
| 4,292,689 | * | 10/1981 | Townsend, Jr. | 2/12 |
| 5,024,262 | | 6/1991 | Huang . | |
| 5,471,684 | * | 12/1995 | Casale | 2/195.1 |
| 5,548,846 | * | 8/1996 | Bianchetti | 2/209.12 |

FOREIGN PATENT DOCUMENTS 1562282   3/1980   (GB) .

* cited by examiner

Primary Examiner—John J. Calvert
Assistant Examiner—Katherine Moran
(74) Attorney, Agent, or Firm—Boniard I. Brown

(57) ABSTRACT

A visor for a head of a person has a closed spring-like loop, a flexible web mounted thereon to define a visor portion, and a head opening. The loop is twistable to form a pair of smaller loops for transport or storage.

6 Claims, 2 Drawing Sheets

FIG.—1
FIG.—2
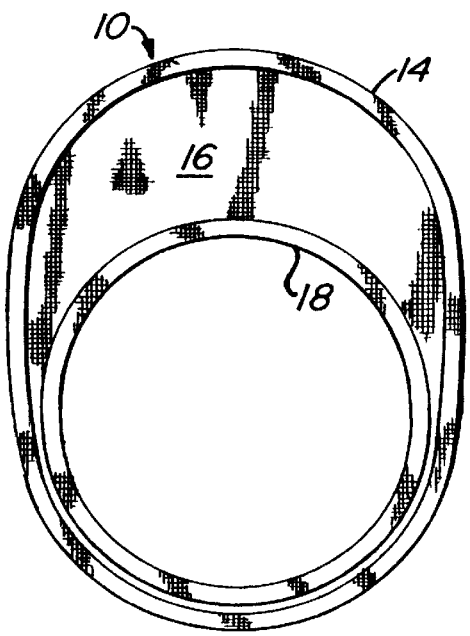
FIG.—3
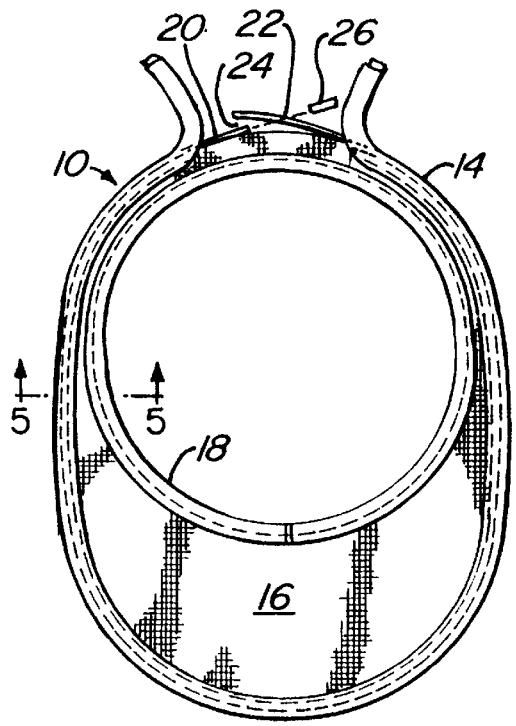
FIG.—4
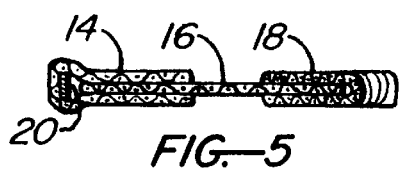
FIG.—5

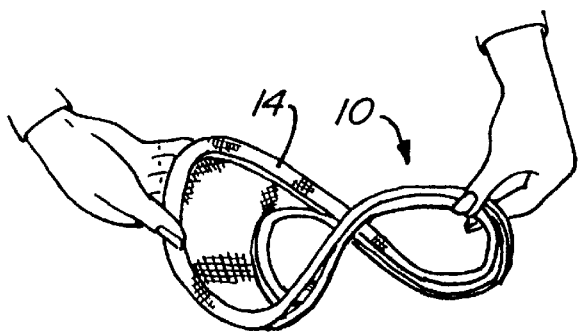
FIG.—6
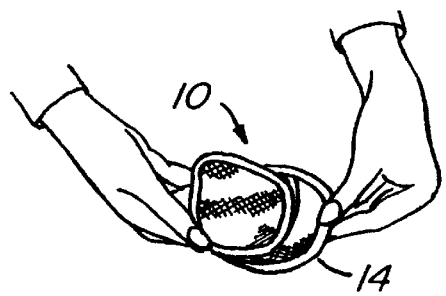
FIG.—7
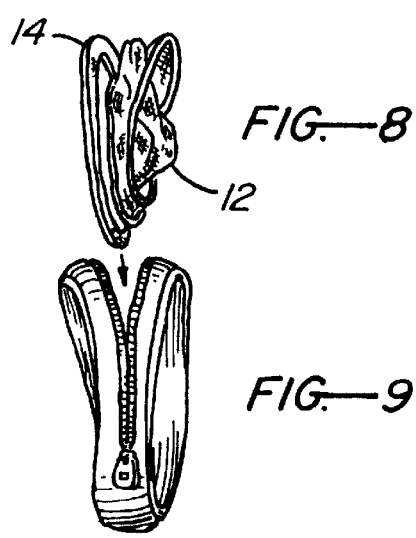
FIG.—8
FIG.—9

COLLAPSIBLE VISOR FOR HEAD WEAR

BACKGROUND & SUMMARY OF THE INVENTION

The present invention relates to visors for wear on the head of a person and more particularly to a visor of simplified construction which is readily contracted to a compact configuration.

The invention provides a visor for the head of a wearer, comprising a closed loop of spring-like material of generally oval configuration when extended, and a flexible web mounted on the loop and defining an opening to receive the head of the wearer. The loop is twistable to form a pair of smaller loops foldable in layered array in compact configuration for carrying and storage. The loop is enclosed in a peripheral hem of the visor.

BRIEF DESCRIPTION OF THE DRAWINGS

FIG. 1 is a perspective view of a visor according to the invention having an open top and disposed on a wearer's head;

FIG. 2 is a perspective view of a visor of the invention disposed on the head of a wearer and having an enclosed cap portion;

FIG. 3 is a plan view of a preferred form of the visor of the invention;

FIG. 4 is a plan view, partially exploded, of a visor according to the invention showing hem portions and end portions of a loop component;

FIG. 5 is a sectional view taken at line 5—5 in FIG. 4;

FIG. 6 is a perspective view showing manual twisting of the visor of FIG. 3 by grasping opposite side portions;

FIG. 7 is a view showing the folding of the visor of the invention into compact layered configuration;

FIG. 8 is a side view showing the folded visor compacted for carrying or storage; and FIG. 9 is a side view of a carrying case for the compact visor.

DESCRIPTION OF THE PREFERRED EMBODIMENT

FIGS. 1 to 3 illustrate a preferred embodiment of the visor of the invention. FIG. 1 shows a visor 10 disposed on the head of a person and having an open top, and FIG. 2 shows a visor on the head of a person and having a fabric cap portion 12 extending over the head of the person.

FIG. 3 shows, in plan view, visor 10 as comprising an outer loop 14, a fabric portion 16, and an inner, somewhat oval opening defined by a stretchable head band 18.

A loop or band 20 (FIGS. 4 and 5), typically fabricated of spring steel or of appropriate plastic, maintains the visor in the extended configuration of FIG. 3. The loop end portions 22, 24 are joined, as by clamp member or fastener 26, by welding, soldering, or by appropriate adhesive.

The loop 20 is enclosed in a continuous peripheral hem or sleeve 14, formed as a fabric, such as nylon, plastic-coated fabric, etc., with the loop being inserted in the tube or sleeve and extending therethrough.

A hem 18 is disposed about a somewhat oval opening and is formed of a stretchable material to fit about the heads of wearers of different sizes.

A visor portion 16 is defined by the flexible fabric portion 16, and serves to shield the eyes of a wearer.

From its open, extended configuration of FIG. 3, the visor is twistable into the configuration of FIGS. 7 and 8, by manually grasping diametrically opposite sides thereof (FIG. 6) and twisting the opposite sides toward each other, then folding the sides toward each other, as indicated in FIG. 7, bringing the hands together to dispose the sides one above the other in layered configuration. Two loops are thus super-imposed or overlaid, the overlaid loops having a diameter of about one-third the diameter of the fully extended visor of FIG. 3. Thus folded, the visor is readily positioned or disposed in a pocket, purse, etc., for carrying or for storage purposes, as indicated in FIGS. 8 and 9.

It will be understood that various changes and modifications may be made from the preferred embodiments discussed above without departing from the scope of the present invention, which is established by the following claims and equivalents thereof.

The inventor claims:

1. A visor for the head of a wearer, comprising:
   a closed loop of a spring-like material, said loop being of generally oval configuration when extended,
   a flexible web mounted on said loop and extending inwardly therefrom,
   a visor portion defined by said web for shielding the eyes of a wearer,
   said flexible web has a generally oval opening defined therein to accommodate the head of a wearer, said flexible hem member being stretchable to accommodate different sizes of heads of wearers, and
   said visor loop being deployable in said generally oval configuration, and being twistable into a compact layered array by twisting opposite side portions of the loop to twist the loop into two generally symmetrical loops superimposed relative to each other.

2. A visor according to claim 1, and further comprising a cap portion to extend over the head of the wearer.

3. A visor according to claim 1, wherein said loop is formed of one of (a) spring steel, (b) appropriate spring plastic.

4. A visor according to claim 1, wherein said loop comprises a metal wire.

5. A visor according to claim 1, wherein said loop is enclosed in a peripheral hem of said flexible web.

6. A visor according to claim 1, wherein said web is formed of one of (a) synthetic fabric, (b) plastic-coated fabric, (c) plastic sheet, (d) stretch fabric.

* * * * *